United States Patent
Hirahara et al.

(10) Patent No.: US 8,940,673 B2
(45) Date of Patent: Jan. 27, 2015

(54) SKIN CLEANSING COMPOSITION

(71) Applicant: Kao Corporation, Tokyo (JP)

(72) Inventors: Mayuko Hirahara, Bunkyo-ku (JP); Koji Endo, Katsushika-ku (JP); Kenji Kaneda, Adachi-ku (JP); Masahiro Miyaki, Higashimurayama (JP)

(73) Assignee: Kao Corporation, Tokyo (JP)

( * ) Notice: Subject to any disclaimer, the term of this patent is extended or adjusted under 35 U.S.C. 154(b) by 1 day.

(21) Appl. No.: 13/727,336

(22) Filed: Dec. 26, 2012

(65) Prior Publication Data

US 2014/0080747 A1  Mar. 20, 2014

(30) Foreign Application Priority Data

Sep. 20, 2012  (JP) ................. 2012-207618

(51) Int. Cl.
    *A61K 8/00* (2006.01)
    *A61K 8/46* (2006.01)
    *A61K 8/36* (2006.01)

(52) U.S. Cl.
    CPC . *A61K 8/466* (2013.01); *A61K 8/36* (2013.01); *A61K 8/46* (2013.01)
    USPC ........... 510/130; 510/424; 510/426; 510/428; 510/492

(58) Field of Classification Search
None
See application file for complete search history.

(56) References Cited

U.S. PATENT DOCUMENTS

| | | | |
|---|---|---|---|
| 5,078,916 A | 1/1992 | Kok et al. | |
| 5,632,978 A | 5/1997 | Moore et al. | |
| 5,866,110 A | 2/1999 | Moore et al. | |
| 2003/0185783 A1 | 10/2003 | Terazaki | |
| 2003/0232029 A1 | 12/2003 | Terazaki | |
| 2007/0031362 A1 | 2/2007 | Kreeger et al. | |
| 2007/0086970 A1 | 4/2007 | Terazaki | |
| 2008/0242581 A1* | 10/2008 | Murphy et al. | 510/414 |
| 2008/0261845 A1 | 10/2008 | Yamamoto et al. | |
| 2009/0075854 A1 | 3/2009 | Terazaki | |
| 2012/0039835 A1 | 2/2012 | Terazaki | |

FOREIGN PATENT DOCUMENTS

| | | |
|---|---|---|
| JP | 1-151510 A | 6/1989 |
| JP | 2003-81935 A | 3/2003 |
| JP | 2003-252731 A | 9/2003 |
| JP | 2003-252732 A | 9/2003 |
| JP | 2006-527785 A | 12/2006 |
| JP | 2007-15940 A | 1/2007 |
| JP | 2008-285479 A | 11/2008 |
| JP | 4225673 B2 | 2/2009 |
| WO | WO 96/05798 A1 | 2/1996 |

OTHER PUBLICATIONS

Imokawa, "Chapter 19: Surfactant Mildness," Surfactants in Cosmetics—Second Edition, pp. 427-471, 1997, Marcel Dekker, Inc., New York, New York, USA.
The Non-Final Office Action for related U.S. Appl. No. 13/727,342, dated Apr. 14, 2014.

\* cited by examiner

*Primary Examiner* — Necholus Ogden, Jr.
(74) *Attorney, Agent, or Firm* — Birch, Stewart, Kolasch & Birch, LLP

(57) ABSTRACT

The present invention provides a skin cleansing composition comprising the following components (A), (B), and (C):
  (A) (a1) an alkenylsulfonic acid having 12 to 22 carbon atoms or its salt, (a2) an alkylsulfonic acid having 12 to 22 carbon atoms or its salt, or a mixture of them,
  (B) an alkyl ether carboxylic acid represented by the following formula (1) or its salt:

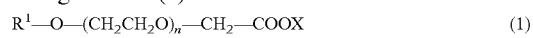

$$R^1-O-(CH_2CH_2O)_n-CH_2-COOX \quad (1)$$

wherein $R^1$ represents an alkyl group having 4 to 22 carbon atoms, n denotes a number from 0 to 20, X represents a hydrogen atom, an alkali metal, an alkali earth metal, ammonium, or organic ammonium, and n denotes a number of 0.5 or more and less than 4 on average; and
  (C) water.

18 Claims, No Drawings

SKIN CLEANSING COMPOSITION

FIELD OF THE INVENTION

The present invention relates to a skin cleansing composition.

BACKGROUND OF THE INVENTION

In the Asian region including Japan, soap constitutes the mainstream of skin cleansing agents such as whole body cleansing agents from of old. Consumers in this region prefer soap having a good squeaky feeling in rinsing besides good foaming tendency and creamy foam qualities (Surfactants in Cosmetics, Second Edition PP427).

In the meantime, an alkyl ether sulfate is used as skin cleansing agents such as whole body agents in, primarily, Europe and America. Because the alkyl ether sulfate has bubbly foam qualities, giving a slimy feeling in rinsing, Europeans and Americans prefer this. Also, because the alkyl ether sulfate is relatively more moderate to the skin than soap, it is also widely used in Japan (WO96/05798 A). JP 2003-81935 A discloses a specific internal olefin sulfonate with the intention of obtaining solubilization ability, penetration ability, and surface tension-lowering ability and describes that when the olefin sulfonate is used for shampoos, good foaming properties and good feeling to the touch are obtained without any squeaky feeling during shampooing.

Also, an alkyl ether carboxylic acid surfactant is known as a surfactant having low irritation to the skin. However, it has less foamability and therefore studies are being made concerning a method of combining it with other surfactants such as an alkyl ether sulfate (JP 2008-285479 A).

SUMMARY OF THE INVENTION

The present invention relates to a skin cleansing composition comprising the following components (A), (B), and (C):

(A) (a1) an alkenylsulfonic acid having 12 to 22 carbon atoms or its salt, or (a2) an alkylsulfonic acid having 12 to 22 carbon atoms or its salt, or a mixture of them;

(B) an alkyl ether carboxylic acid represented by the following formula (1) or its salt:

$$R^1-O-(CH_2CH_2O)_n-CH_2-COOX \qquad (1)$$

wherein $R^1$ represents an alkyl group having 4 to 22 carbon atoms, n denotes a number from 0 to 20, X represents a hydrogen atom, an alkali metal, an alkali earth metal, ammonium, or organic ammonium, and n denotes a number of 0.5 or more and less than 4 on average; and (C) water.

DETAILED DESCRIPTION OF THE INVENTION

Although usual fatty acid soap detergents are preferred because they have a refresh feeling during rinsing, they have the problems that they each have a high pH and tend to give a taut feeling to the washed skin. Because the alkyl ether sulfate has bubbly foam qualities, giving a slimy feeling in rinsing, it has a problem that it is less acceptable to Japanese and peoples in Asian countries.

The present invention relates to a skin cleansing composition which is superior in foam qualities and foam volume, can reduce slimy feeling in rinsing, can impart a squeaky feeling similar to that of soap and can also provide washed skin a good feel pleasant to the touch.

The inventors of the present invention have found that a skin cleansing composition which is superior in foam qualities and foam volume, has a high detergency, can also impart a squeaky feeling similar to that of soap in rinsing, and can provide washed skin a good feel pleasant to the touch can be obtained by using a combination of a specific alkenylsulfonic acid or its salt, an alkylsulfonic acid or its salt, or a mixture of them and a specific alkyl ether carboxylic acid or its salt.

The skin cleansing composition of the present invention is superior in foam qualities and foam volume, can reduce slimy feeling in rinsing, can also impart a squeaky feeling similar to that of soap and can provide washed skin a good feel pleasant to the touch without providing a taut feeling.

Component (A) used in the present invention is (a1) an alkenylsulfonic acid having 12 to 22 carbon atoms or its salt, (a2) an alkylsulfonic acid having 12 to 22 carbon atoms or its salt, or a mixture of them.

The above (a1) will be explained in detail. (a1) is an alkenylsulfonic acid having 12 to 22 carbon atoms or its salt, and preferably an alkenylsulfonic acid which is a straight-chain hydrocarbon having a double bond and 12 to 22 carbon atoms, and more preferably an alkenylsulfonic acid which is a straight-chain hydrocarbon having a double bond and 12 to 18 carbon atoms and containing a sulfo-group on any one of the carbon atoms excluding terminal carbon atoms or its salt. (a1) is even more preferably an alkenylsulfonic acid which is a straight-chain hydrocarbon having double bonds and 12 to 18 carbon atoms, wherein the double bonds located at the third or upper positions in the inside of the straight-chain hydrocarbon are contained at 70% by mass or more, and also containing a sulfo-group on any one of the carbon atoms excluding terminal carbon atoms or its salt.

The alkenylsulfonic acid having 12 to 22 carbon atoms or its salt may be used either alone or in combination with two or more and it is preferable to use a combination with two or more of alkenylsulfonic acids corresponding to the purpose of use from the point that foam volume and foam qualities can be controlled. Among them, an alkenylsulfonic acid having 16 or 18 carbon atoms or its salt is preferable from the point of foam volume and foam qualities. Also, the alkenylsulfonic acids having 16 and 18 carbon atoms or their salts are preferably used as a mixture thereof and the ratio by mass of the alkenylsulfonic acid having 16 carbon atoms or its salt to the alkenylsulfonic acid having 18 carbon atoms or its salt is preferably 1/9 to 9/1, more preferably 2/8 to 8/2, and even more preferably 5/5 to 2/8. This enables an improved feeling to the touch in rinsing.

The above (a2) will be explained in detail. (a2) is an alkylsulfonic acid having 12 to 22 carbon atoms or its salt, preferably a hydroxyalkylsulfonic acid having 12 to 22 carbon atoms or its salt, and more preferably a hydroxyalkylsulfonic acid having 12 to 22 carbon atoms and containing a sulfo-group on any one of the carbon atoms excluding terminal carbon atoms or its salt, and even more preferably a hydroxyalkylsulfonic acid having 12 to 18 carbon atoms and containing a sulfo-group on any one of the carbon atoms excluding terminal carbon atoms or its salt. (a2) is even more preferably a hydroxyalkylsulfonic acid which is a straight-chain hydrocarbon having 12 to 18 carbon atoms and containing a hydroxyl group on any one of the carbon atoms excluding terminal carbon atoms and containing a sulfo-group on any one of the carbon atoms excluding terminal carbon atoms or its salt.

The hydroxyalkylsulfonic acid having 12 to 22 carbon atoms or its salt may be used either alone or in combination with two or more and it is preferable to use a combination of two or more of hydroxyalkylsulfonic acids or their salts corresponding to the purpose of use from the point that foam volume and foam qualities can be controlled. A hydroxyalkylsulfonic acid having 16 and 18 carbon atoms or its salt is preferable from the point of foam volume and foam qualities. Also, these hydroxyalkylsulfonic acids having 16 and 18 or their salts are preferably used as a mixture and the ratio by mass of the hydroxyalkylsulfonic acid having 16 carbon atoms or its salt to the hydroxyalkylsulfonic acid having 18 carbon atoms or its salt is preferably 1/9 to 9/1, more preferably 2/8 to 8/2 and even more preferably 5/5 to 2/8. This enables an improved feeling to the touch in rinsing.

Component (A) may be either (a1) or (a2), or a mixture of (a1) and (a2). In the case of a mixture of (a1) and (a2), the ratio by mass of (a1) to (a2), (a1)/(a2), is preferably 5/95 to 50/50 and more preferably 10/90 to 30/70.

The ratio by mass of (a1) to (a2) is measured according to the method described in the examples which will be explained later.

Examples of the salts of (a1) and (a2) include those constituted of an alkali metal such as sodium or potassium; alkali earth metal such as calcium or magnesium; ammonium; or organic ammonium generated from monoethanolamine, diethanolamine, or triethanolamine and the like. Among these salts, an alkali metal salt or ammonium salt is preferable from the point of temperature stability and resistance to coloring with time.

Moreover, component (A) is preferably a mixture of (a1) an alkenylsulfonic acid containing a sulfo-group on any one of the carbon atoms excluding terminal carbon atoms and having 12 to 22 carbon atoms or its salt and (a2) a hydroxyalkylsulfonic acid which is a straight-chain hydrocarbon containing a hydroxyl group and having 12 to 22 carbon atoms and contains a sulfo-group on any one of the carbon atoms excluding terminal carbon atoms or its salt.

Component (A) is a mixture of (a1) an alkenylsulfonic acid containing a sulfo-group on any one of the carbon atoms excluding terminal carbon atoms and having 16 carbon atoms or its salt and (a2) a hydroxyalkylsulfonic acid which is a straight-chain hydrocarbon containing a hydroxyl group and having 16 carbon atoms and contains a sulfo-group on any one of the carbon atoms excluding terminal carbon atoms or its salt or;

preferably a mixture of (a1) an alkenylsulfonic acid containing a sulfo-group on any one of the carbon atoms excluding terminal carbon atoms and having 18 carbon atoms or its salt and (a2) a hydroxyalkylsulfonic acid which is a straight-chain hydrocarbon containing a hydroxyl group and having 18 carbon atoms and contains a sulfo-group on any one of the carbon atoms excluding terminal carbon atoms or its salt; or more preferably a mixture of (a1) a mixture of alkenylsulfonic acids each containing a sulfo-group on any one of the carbon atoms excluding terminal carbon atoms and having 16 and 18 carbon atoms or their salts and (a2) a mixture of hydroxyalkylsulfonic acids which are each a straight-chain hydrocarbon containing a hydroxyl group and having 16 and 18 carbon atoms and each contain a sulfo-group on any one of the carbon atoms excluding terminal carbon atoms or their salts.

Moreover, component (A) is preferably a mixture of (a1) a mixture of an alkenylsulfonic acids each containing a sulfo-group on any one of the carbon atoms excluding terminal carbon atoms and having 16 and 18 carbon atoms or their salts and (a2) a mixture of hydroxyalkylsulfonic acids which are each a straight-chain hydrocarbon containing a hydroxyl group and having 16 and 18 carbon atoms and each contains a sulfo-group on any one of the carbon atoms excluding terminal carbon atoms or their salts, wherein mixing ratio by mass of the hydrocarbon having 16 carbon atoms to the hydrocarbon having 18 carbon atoms is preferably 9/1 to 1/9, more preferably 8/2 to 2/8, and even more preferably 5/5 to 2/8, and the ratio by mass of (a1) to (a2) is preferably 5/95 to 50/50 and more preferably 10/90 to 30/70 from the point of a feeling to the touch in rinsing.

The sulfonic acid or its salt which is component (A) can be obtained by sulfonating a starting raw material which is an alkene having 12 to 22 carbon atoms, followed by neutralizing and hydrolyzing. No particular limitation is imposed on the conditions of sulfonation, neutralization, and hydrolysis, and these conditions may be determined on referring to the method described in Tenside Surf. Det. 31 (5), 299, (1994).

When the sulfonic acid or its salt which is component (A) is produced, a process involving sulfonation, neutralization, and hydrolysis may be performed either by using a raw material alkene having a carbon number distribution ranging from 12 to 22, by using a raw material alkene having a single carbon number, or by using a mixture of a lot of sulfonates which are produced in advance and each have different carbon number as needed.

As component (A), one or two or more types may be used and the content of component (A) is preferably 0.1% by mass or more, more preferably 0.5% by mass or more, even more preferably 1% by mass or more, preferably 60% by mass or less, more preferably 30% by mass or less, even more preferably 20% by mass or less, and even more preferably 15% by mass or less on salt basis in a total composition from the viewpoint of foamability and foam volume. Also, component (A) is contained in an amount of preferably 0.1 to 60% by mass, more preferably 0.5 to 30% by mass, even more preferably 1 to 20% by mass, and even more preferably 1 to 15% by mass in a total composition.

Component (B) is an alkyl ether carboxylic acid represented by the above formula (1) or its salt.

In the formula, $R^1$ is an alkyl group having 4 to 22 carbon atoms, preferably an alkyl group having 6 to 20 carbon atoms, more preferably an alkyl group having 8 to 18 carbon atoms, even more preferably an alkyl group having 8 to 16 carbon atoms, and even more preferably an alkyl group having 10 to 16 carbon atoms. Also, $R^1$ is preferably a straight-chain alkyl group from the viewpoint of foamability, though the alkyl chain of $R^1$ may be any of a straight chain or branched chain. Also, the average carbon number of $R^1$ is preferably 10.8 to 12.8, more preferably 10.8 to 12.5, and even more preferably 12.1 to 12.4 from the viewpoint of foamability, foam qualities, and low-temperature stability.

Also, $R^1$ preferably has two or more types of alkyl groups, and in $R^1$, a component having an alkyl chain length which is contained at a highest amount in the composition is preferably 55% by mass or more and less than 97% by mass, more preferably 60 to 95% by mass, and even more preferably 70 to 95% by mass from the point of excellent foam volume and foam qualities.

Also, in the formula, n denotes a number of 0 to 20 and preferably 0 to 12. In this case, n denotes the number of moles of added ethylene oxide and the average number (average of ns) of moles of added ethylene oxide of component (B) is 0.5 or more and less than 4, preferably 1 or more, more preferably 2 or more, even more preferably 2.5 or more, more preferably 3.8 or less, more preferably 3.4 or less, and even more preferably 3.1 or less from the viewpoint of excellent foam qualities.

The alkyl ether carboxylic acid or its salt which is component (B) contains a component obtained when n=0 in the formula (1) in an amount of preferably 9.9 to 27% by mass, more preferably 9.9 to 16% by mass, and even more preferably 9.9 to 15% by mass from the point of improving a squeaky feel in rinsing.

Moreover, the total content of components (n=1 and 2) is preferably less than 40% by mass, more preferably 20 to 37% by mass, even more preferably 27 to 36.5% by mass, and even more preferably 35 to 36.1% by mass from the viewpoint of foam qualities and foam volume.

Examples of X in the formula include a hydrogen atom; alkali metals such as sodium and potassium; alkali earth metals such as calcium and magnesium; ammonium; alkanol amines such as monoethanolamine, diethanolamine, and triethanolamine, and organic amines. Among these compounds, alkali metals are preferable from the point of foamability, low-temperature characteristics, and resistance to coloring with time.

The alkyl ether carboxylic acid or its salt which is component (B) is preferably a mixture of components (n=0, 1, 2, 3, and 4) each represented by the formula (1) in which the ratio by mass of these components (n=0, 1, 2, 3, and 4) are preferably as follows from the point of the compatibility between foamability, detergency, and squeaky feeling: (mass of the component (n=0)):(mass of the component (n=1)):(mass of the component (n=2)):(mass of the component (n=3)):(mass of the component (n=4))=1:0.99 to 3.50:0.89 to 3.00:0.76 to 3.00:0.63 to 1.6.

Component (B) is preferably those which contain a component (n=0) represented by the formula (1) in an amount of 9.9% by mass or more and less than 12% by mass and in which the ratio of (mass of the component (n=0)):(mass of the component (n=1)):(mass of the component (n=2)):(mass of the component (n=3)):(mass of the component (n=4))=1:1.53 to 1.87:1.59 to 2.25:1.33 to 2.16:1.14 to 1.52 or those which contain a component (n=0) represented by the formula (1) in an amount of 12% by mass to 17% by mass and in which the ratio of (mass of the component (n=0)):(mass of the component (n=1)):(mass of the component (n=2)):(mass of the component (n=3)):(mass of the component (n=4))=1:0.99 to 1.34: 0.89 to 1.40:0.76 to 1.23:0.63 to 0.99 from the point of foamability and rinsing ability.

Component (B) is preferably those which contain a component (n=0) represented by the formula (1) in an amount of 9.9% by mass to 11.5% by mass and in which the ratio of (mass of the component (n=0)):(mass of the component (n=1)):(mass of the component (n=2)):(mass of the component (n=3)):(mass of the component (n=4))=1:1.58 to 1.84: 1.72 to 2.17:1.49 to 2.00:1.14 to 1.52 or those which contain a component (n=0) represented by the formula (1) in an amount of 13% by mass to 17% by mass and in which the ratio of (mass of the component (n=0)):(mass of the component (n=1)):(mass of the component (n=2)):(mass of the component (n=3)):(mass of the component (n=4))=1:1.00 to 1.31: 0.93 to 1.34:0.79 to 1.18:0.63 to 0.99 from the point of foam volume, foam qualities, and rinsing ability.

In component (B) represented by the formula (1), preferably, $R^1$ in the formula (1) is an alkyl group having 8 to 18 carbon atoms and the average carbon number of $R^1$ is 10.8 to 12.8, the amount of a component having an alkyl chain length which is contained at a highest amount in the composition of $R^1$ is 55% by mass or more and less than 97% by mass, moreover, n denotes a number from 0 to 20, the average of ns is 2.5 to 3.4, a component (n=0) is contained in an amount of 9.9 to 27% by mass, and the total content of a component (n=1) and a component (n=2) is 20 to 37% by mass. Also, as X in the formula, a hydrogen atom, sodium, potassium, or ammonium is preferable. Such a structure can promote foamability.

In component (B) represented by the formula (1), preferably, $R^1$ in the formula (1) is an alkyl group having 8 to 18 carbon atoms and the average carbon number of $R^1$ is 10.8 to 12.8, the amount of a component having an alkyl chain length which is contained at a highest amount in the composition of $R^1$ is 55% by mass or more and less than 97% by mass, moreover, n denotes a number from 0 to 20, the average of ns is 2.5 to 3.4, a component (n=0) is contained in an amount of 9.9 to 27% by mass, and the total content of a component (n=1) and a component (n=2) is 27 to 36.5% by mass. Also, as X in the formula, a hydrogen atom, sodium, potassium, or ammonium is preferable. Such a structure can promote stop feeling characteristics in rinsing.

In component (B) represented by the formula (1), preferably, $R^1$ in the formula (1) is an alkyl group having 8 to 16 carbon atoms and the average carbon number of $R^1$ is 10.8 to 12.5, the amount of a component having an alkyl chain length which is contained at a highest amount in the composition of $R^1$ is 60% by mass to 95% by mass, moreover, n denotes a number from 0 to 20, the average of ns is 2.8 to 3.4, a component (n=0) is contained in an amount of 9.9 to 27% by mass and preferably 9.9 to 16% by mass, and the total content of a component (n=1) and a component (n=2) is 27 to 36.5% by mass. Also, as X in the formula, a hydrogen atom, sodium, potassium, or ammonium is preferable. Such a structure can improve foam volume and foam qualities.

In component (B) represented by the formula (1), preferably, $R^1$ in the formula (1) is an alkyl group having 10 to 16 carbon atoms and the average carbon number of $R^1$ is 12.1 to 12.4, the amount of a component having an alkyl chain length which is contained at a highest amount in the composition of $R^1$ is 60% by mass to 95% by mass, moreover, n denotes a number from 0 to 20, the average of ns is 2.8 to 3.1, a component (n=0) is contained in an amount of 9.9 to 15% by mass, and the total content of a component (n=1) and a component (n=2) is 35 to 36.1% by mass. Also, as X in the formula, a hydrogen atom, sodium, potassium, or ammonium is preferable. Such a structure can improve foam volume and foam qualities.

In component (B) in the present invention, the distribution of alkyl chain length of $R^1$, the average alkyl chain of $R^1$, the amount of a component (n=0), the average addition mole number of n, and the ratio by mass of components (n=0, 1, 2, 3, and 4) are found in the following manner by analyzing an alkyl ether carboxylic acid represented by the formula (1) according to a gas chromatographic method.

[Distribution of Alkyl Chain Length of $R^1$]

Among the peak areas obtained by gas chromatography, the peak area of each alkyl chain length corresponding to n=0 was found to define the sum of peak areas as 100, thereby finding the percentage of the distribution of each alkyl chain length. With regard to n=1 to 3, the percentage of the distribution of each alkyl chain length was found by the same calculation as above to calculate an average of the percentages of the alkyl chain distributions obtained when n=0 to 3, thereby finding the distribution of alkyl chain length of $R^1$ (from this, an alkyl group component which is contained at a highest amount in the composition of $R^1$ can be specified).

[Average Alkyl Chain Length of $R^1$]

The ratio of each component was found from the distribution of alkyl chain length of $R^1$ found in the above manner and multiplied by the number of carbons corresponding to the alkyl chain length equivalent to each obtained ratio to obtain the sum of the obtained products. This obtained sum was defined as an average alkyl chain length.

[Amount of a Component (n=0), Total Content of Components (n=1 and 2)]

The chain length of the alkyl group which is contained at a highest amount in the composition of $R^1$ was specified to calculate the sum of the areas of gas chromatography corresponding to n=0 to 10 of the component having the alkyl chain length. The total amount was defined as 100% to calculate the amount of a component obtained when n=0 and the total content of components obtained when n=1 and 2.

[Average Addition Mole Number of n]

The chain length of the alkyl group which is contained at a highest amount in the composition of $R^1$ was specified to calculate the sum of the areas of gas chromatography corresponding to n=0 to 10 of the component having the alkyl chain length (in this case, the amount of a component (n=11 or more) was very small and was therefore excluded in the calculation). This total amount was defined as 1 to calculate the ratio of each component (n=0 to 10). This ratio was multiplied by each addition mole number and the sum of each addition mole number was defined as the average addition mole number of n.

[Ratio by Mass of Components (n=0, 1, 2, 3, and 4)]

With regard to the ratio of each component differing in EO addition mole number, the distribution of alkyl chain length of $R^1$ was found by the method shown above to specify a component having a chain length of the alkyl group which is contained at a highest amount in the composition of $R^1$, and the ratio by mass of components (n=0, 1, 2, 3, and 4) was determined from the ratio of the areas of the components (n=0, 1, 2, 3, and 4) which is contained at a highest amount in the composition.

The alkyl ether carboxylic acid or its salt which is component (B) has the composition mentioned above and the content of component (B) is preferably 0.1% by mass or more, more preferably 0.5% by mass or more, even more preferably 1% by mass or more, preferably 30% by mass or less, more preferably 20% by mass or less, and even more preferably 15% by mass or less on acid basis in a total composition from the viewpoint of detergency, foam volume, and foam qualities. Also, component (B) is contained in an amount of preferably 0.1 to 30% by mass, more preferably 0.5 to 20% by mass, and even more preferably 1 to 15% by mass, in a total composition.

In the present invention, the cleansing composition gives no slimy feeling and not only simply imparts a squeaky feeling but also can amazingly generate a squeaky feeling similar to that of soap in rinsing by using a combination of (A) (a1) an alkenylsulfonic acid having 12 to 22 carbon atoms or its salt or (a2) an alkylsulfonic acid having 12 to 22 carbon atoms or its salt, or a mixture of them and (B) an alkyl ether carboxylic acid or its salt (formula (1)). Particularly, the ratio by mass of component (A): component (B) (here, the amount of component (A) indicates the mass when component (A) is in the form of a salt and the amount of component (B) indicates the mass when component (B) is in the form of an acid) is preferably 8:2 to 2:8 and more preferably 8:2 to 5:5, since thereby a squeaky feeling similar to that of soap as above in rinsing can drastically occur and can feel strongly a unique change in terms of a feel to the touch.

In the present invention, water used as component (C) is used as a solvent and may be used as a balance after other components are formulated and may be contained in an amount of preferably 10% by mass or more, more preferably 30% by mass or more, even more preferably 40% by mass or more, preferably 80% by mass or less, more preferably 70% by mass or less, and even more preferably 60% by mass or less in a total composition.

The skin cleansing composition of the present invention may further comprise a component (D), for example, a polymer having a cationic group, whereby the cleansing composition can be improved in foam qualities and foam volume.

Examples of the polymer having a cationic group include polymers containing dimethyldiallylammonium chloride as a monomer. Specific examples of these polymers include homopolymers of dimethyldiallylammonium chloride; copolymers of dimethyldiallylammonium chloride and other monomers such as a (meth)acrylic acid, (meth)acrylate, or (meth)acrylamide; and polychlorinated methacryloyloxyethyltrimethylammonium chloride. Other examples include cationic cellulose and cationic guar gum.

In more detail, specific examples of the polymer having a cationic group include homopolymers of dimethyldiallylammonium chloride (Merquat 100 (trademark); manufactured by Lubrizol Corporation), copolymers of dimethyldiallylammonium chloride and acrylic acid (Merquat 295 (trade mark), manufactured by Lubrizol Corporation), copolymers of dimethyldiallylammonium chloride and acrylic acid (Merquat 280 (trade mark); manufactured by Lubrizol Corporation), copolymers of dimethyldiallylammonium chloride and acrylamide (Merquat 550 (trade mark), manufactured by Lubrizol Corporation), copolymers of dimethyldiallylammonium chloride, acrylic acid, and acrylamide (Merquat PLUS 3330, 3331 (trade mark), manufactured by Lubrizol Corporation), and polychlorinated methacryloyloxyethyltrimethylammonium chloride (manufactured by Kao Corporation).

Examples of the cationic cellulose include a salt of hydroxyethylcellulose which is obtained by a reaction between hydroxyethylcellulose and trimethylammonium substituted epoxide and called Polyquaternium 10. Specific examples of the cationic cellulose include compounds commercially available under the names of Polymer KG, JR, and LR Series (Polymer RL400, Polymer KG-30M) from Amerchol Corp.

Examples of the cationic guar gum include guar hydroxypropyl trimonium chloride. Specific examples of the cationic guar gum include compounds commercially available under the name of Jaguar Series (preferably Jaguar C-17) from Rhodia Inc., and compounds commercially available under the name of N-Hance Polymer Series from Aqualon Company.

Among these compounds, copolymers of dimethyldiallylammonium chloride and acrylamide (Merquat 550 (trade mark), manufactured by Lubrizol Corporation) and copolymers of dimethyldiallylammonium chloride, acrylic acid, and acrylamide (Merquat 3331 (trademark), manufactured by Lubrizol Corporation), Polymer RL400 as the cationic cellulose and Jaguar C-17 as the cationic guar gum can produce, particularly, a high effect on improvements in foam volume and foam qualities.

The content of the cationic group-containing polymer which is component (D) is preferably 0.01% by mass or more, more preferably 0.05% by mass or more, even more preferably 0.1% by mass or more in a total composition, preferably 2% by mass or less, more preferably 1% by mass or less, and even more preferably 0.5% by mass from the viewpoint of improving foam volume and foam qualities and also from the point of the viscosity of the composition. Also, component (D) is contained in an amount of preferably 0.01 to 2% by mass, more preferably 0.05 to 1% by mass, and even more preferably 0.1 to 0.5% by mass in a total composition.

The cationic polymer which is component (D) can impart a specific feeling to the dried skin by the combined use of components (A) and (B). Specifically, the cationic polymer can impart to the skin after dried, a skin feeling like silk in which a slippery feeling and moist feeling are compatible with each other. Particularly, the ratio by mass of component (D) to the total mass of components (A) and (B) (where the mass of component (A) indicates the mass when component (A) is in the form of a salt and the mass of component (B) indicates the mass when component (B) is in the form of an acid) is preferably in the following range: (D)/((A)+(B))=0.001 to 0.05 and more preferably in the following range: (D)/((A)+(B))=0.005 to 0.03.

The skin cleansing composition of the present invention may further comprise component (E) glyceryl ether containing an alkyl group or alkenyl group having 4 to 12 carbon atoms, thereby enabling increase in foam volume in rinsing and prevention of a sticky feeling when the skin is dried.

Examples of the alkyl group or alkenyl group having 4 to 12 carbon atoms include n-butyl group, isobutyl group, tert-butyl group, n-pentyl group, isopentyl group, n-hexyl group, isohexyl group, n-heptyl group, n-octyl group, 2-ethylhexyl group, n-nonyl group, n-decyl group, and n-lauryl group. Among these groups, those having 4 to 11 carbon atoms are preferable, those having 6 to 10 carbon atoms are more preferable, those having one alkyl group having 8 carbon atoms are even more preferable, and 2-ethylhexylglyceryl ether is even more preferable from the viewpoint of difficulty precipitating at low temperature and high foamability.

One or two or more types of component (E) may be used and the content of component (E) is preferably 0.03 to 5% by mass, more preferably 0.06 to 4% by mass, and even more preferably 1 to 4% by mass in a total composition from the viewpoint of suppressing a sticky feeling when the skin is dried and increasing foam volume.

The skin cleansing composition of the present invention may further comprise component (F) an amphoteric surfactant.

Examples of the amphoteric surfactant, include acetic acid betaine type surfactants such as lauryldimethylaminoacetic acid betaine, amine oxide type surfactants such as lauryldimethylamine oxide, imidazolinium betaine type surfactants such as 2-alkyl-N-carboxymethyl-N-hydroxyethylimidazolinium betaine, amide betaine type surfactants such as lauric acid amidepropyl betaine, and sulfobetaine type surfactants such as laurylhydroxysulfobetaine.

One or two or more types of components (F) may be used and are contained in an amount of preferably 0.1 to 20% by mass, 0.5 to 15% by mass, and even more preferably 1 to 10% by mass in a total composition from the point of improving foam qualities and foam volume.

The skin cleansing composition of the present invention may further comprise components which are used in usual detergents, for example, a surfactant other than components (A), (B), (E), and (F), oily component, disinfectant, anti-inflammatory agent, antiseptic, chelating agent, thickener, salts, pearling agent, scrubbing agent, perfumes, chilling agent, dyes, ultraviolet absorber, antioxidant, and vegetable extract.

The skin cleansing composition of the present invention has a pH of preferably 5 to 10, more preferably 5 to 8, and even more preferably 6 to 7. In this case, the pH of the composition is measured at 25° C. after each cleansing composition is diluted 20-fold with ion exchange water.

The skin cleansing composition of the present invention may be produced, for example, in the following manner. Components (A), (B), and (C) are weighed and heated to 80° C. to dissolve uniformly. Other components other than component (D) are further added to the mixture, which is then stirred uniformly, and then, a neutralizing agent (a base) is added to adjust the pH of the solution. Component (D) is added if needed to the mixture, which is then uniformed. Thereafter, a resulting mixture is cooled to 30° C. to obtain a target skin cleansing composition.

The skin cleansing composition of the present invention is suitable as facial cleansers, body soaps, hand soaps, and the like and preferably to body soaps and hand soaps.

A method for washing the skin by using the skin cleansing composition of the present invention is as follows. Specifically, this is a method in which the skin cleansing composition of the present invention is applied in an appropriate amount to the body, that is, the skin of body parts such as a face, arms and legs, and the trunk, then foamed, and washed, followed by rinsing using warm water such as shower. Also, a method may be adopted in which the skin cleansing composition is applied in an appropriate amount to a washing aid such as towel, sponge and brush and then, the cleansing composition is foamed for washing the skin. Moreover, the skin may be washed directly with foam produced by a pump foamer.

The present invention does not limit to the above embodiments, and any change or improvement in the embodiment falls within a scope of the present invention as long as such embodiment can accomplish a purpose of the present invention.

The present invention will be explained in more detail by way of examples, in which the content of each component is expressed by mass %, unless otherwise noted in the following tables. Also, methods for measuring each physical property are as follows.

(I) Production of Component (A)

(1) Measuring Condition (i) Method for Measuring the Position of a Double Bond in an Alkene:

The position of a double bond in an alkene was measured by gas chromatography (hereinafter abbreviated as GC). Specifically, dimethyl disulfide was reacted with the alkene into a dithionate derivative and then, each component was separated by GC. As a result, the position of a double bond in the alkene was found from each peak area.

The instruments and analysis conditions used in the measurement are as follows.

GC instrument: (trade name: HP6890, Hewlett Packard Ltd.)

Column: (trade name: Ultra-Alloy-1HT Capillary Column 30 m×250 μm×0.15 μm, manufactured by Frontier Laboratories Ltd.);

Detector: (Flame Ionization Detector (FID));

Injection temperature: 300° C.;

Detector temperature: 350° C.;

Flow rate of He: 4.6 mL/min.

(ii) Method of Measuring a Ratio by Mass of an Alkenylsulfonate to Hydroxyalkyl Sulfonate:

The ratio by mass of an alkenylsulfonate to hydroxyalkyl sulfonate was measured by HPLC-MS. Specifically, an alkenylsulfonate was separated from hydroxyalkyl sulfonate by HPLC and each was identified by a mass spectrometer (MS). As a result, each ratio was found from the GC-MS peak area.

Instruments and measuring conditions used for the measurement are as follows.
HPLC apparatus (trade name: Agilent Technology 1100, manufactured by Agilent Technologies Inc.);
Column (trade name: L-column ODS 4.6×150 mm, manufactured by (General Incorporated Foundation) Chemical Evaluation and Research Institute, Japan);
Preparation of a sample: (diluted 1000-fold with methanol);
Eluent A (aqueous 10 mM ammonium acetate solution);
Eluent B (10 mM ammonium acetate addition methanol solution) Gradient (0 min. (A/B=30/70%)→10 min. (30/70%)→55 min. (0/100%)→65 min. (0/100%)→66 min. (30/70%)→75 min. (30/70%).
MS Instrument (trade name: Agilent Technology 1100MS SL(G1946D);
MS detection (Detection of negative ions m/z 60-1600, UV240 nm).

(iii) Method for Measuring the Content of a Raw Material Alkene:

The content of the raw material alkene was measured by GC. Specifically, an aqueous solution of a sulfonate having 12 to 22 carbon atoms which was obtained by synthesis was extracted by adding ethanol and petroleum ether to obtain an alkene in the petroleum ether phase. As a result, the amount of an alkene was quantitatively measured from the GC peak area.

The instruments and analysis conditions used in the measurement are as follows.
GC instrument: (trade name: Agilent Technology 6850, manufactured by Agilent Technologies Inc.);
Column: (trade name: Ultra-Alloy-1HT Capillary Column 15 m×250 μm×0.15 μm, manufactured by Frontier Laboratories Ltd.);
Detector: (Flame Ionization Detector (FID));
Injection temperature: 300° C.;
Detector temperature: 350° C.;
Flow rate of He: 3.8 mL/min.

(iv) Method for Measuring the Content of an Inorganic Compound:

The content of an inorganic compound was measured by potentiometry or neutralization titration. Specifically, the content of $Na_2SO_4$ was quantitatively measured by finding the amount of a sulfate radical ($SO_4^{-2}$) by potentiometry. Also, the content of NaOH was measured by neutralization titration using dilute hydrochloric acid.

(2) Production of an Alkene

Production Example A

Synthesis of an Alkene in which the Number of Carbons is 16 and the Content of a Double Bond at C2-Position is 16.5% by Mass A flask equipped with a stirrer was charged with 7000 g (28.9 mol) of 1-hexadecanol (trade name: Kalcol 6098, manufactured by Kao Corporation) and 700 g (10 wt % based on raw material alcohol) of γ-alumina (manufactured by STREM Chemicals, Inc.) as a solid acid catalyst and the mixture was reacted at 280° C. with stirring for 5 hours while flowing nitrogen (7000 mL/min.) in the system. The conversion rate of alcohol after the reaction was finished was 100% and purity of an alkene having 16 carbon atoms was 99.7%. The obtained crude alkene was transferred to a distilling flask to distill at 136 to 160° C./4.0 mmHg, thereby obtaining an alkene having 16 carbon atoms and purity of 100%. The distribution of double bond in the obtained alkene was as follows: C1-position: 0.5% by mass, C2-position: 16.5% by mass, C3-position: 15.4% by mass, C4-position: 16.4% by mass, C5-position: 17.2% by mass, C6-position: 14.2% by mass, and C7-position+C8-position: 19.8% by mass.

Production Example B

Synthesis of an Alkene in which the Number of Carbons is 18 and the Content of a Double Bond at C2-Position was 16.9% by Mass A flask equipped with a stirrer was charged with 7000 g (25.9 mol) of 1-octadecanol (trade name: Kalcol 8098, manufactured by Kao Corporation) and 1050 g (15 wt % based on raw material alcohol) of γ-alumina (manufactured by STREM Chemicals, Inc.) as a solid acid catalyst and the mixture was reacted at 285° C. with stirring for 13 hours while flowing nitrogen (7000 mL/min.) in the system. The conversion rate of alcohol after the reaction was finished was 100% and purity of an alkene having 18 carbon atoms was 98.5%. The obtained crude alkene was transferred to a distilling flask to distill at 148 to 158° C./0.5 mmHg, thereby obtaining an alkene having 18 carbon atoms and purity of 100%. The distribution of double bond in the obtained alkene was as follows: C1-position: 0.7% by mass, C2-position: 16.9% by mass, C3-position: 15.9% by mass, C4-position: 16.0% by mass, C5-position: 14.7% by mass, C6-position: 11.2% by mass, C7-position: 10.2% by mass, and C8-position+C9-position: 14.6% by mass.

Production Example C

Synthesis of an Alkene in which the Number of Carbons is 16 and the Content of a Double Bond at C2-Position is 30.4% by Mass A flask equipped with a stirrer was charged with 7000 g (28.9 mol) of 1-hexadecanol (trade name: Kalcol 6098, manufactured by Kao Corporation) and 700 g (10 wt % based on raw material alcohol) of γ-alumina (manufactured by STREM Chemicals, Inc.) as a solid acid catalyst and the mixture was reacted at 280° C. with stirring for 3 hours while flowing nitrogen (7000 mL/min.) in the system. The conversion rate of alcohol after the reaction was finished was 100% and purity of an alkene having 16 carbon atoms was 99.6%. The obtained crude alkene was transferred to a distilling flask to distill at 136 to 160° C./4.0 mmHg, thereby obtaining an alkene having 16 carbon atoms and purity of 100%. The distribution of double bond in the obtained alkene was as follows: C1-position: 1.8% by mass, C2-position: 30.4% by mass, C3-position: 23.9% by mass, C4-position: 16.8% by mass, C5-position: 12.0% by mass, C6-position: 7.4% by mass, and C7-position+C8-position: 7.8% by mass.

Production Example D

Synthesis of an Alkene in which the Number of Carbons is 18 and the Content of a Double Bond at C2-Position was 31.3% by Mass A flask equipped with a stirrer was charged with 7000 g (25.9 mol) of 1-octadecanol (trade name: Kalcol 8098, manufactured by Kao Corporation) and 700 g (10 wt % based on raw material alcohol) of γ-alumina (manufactured by STREM Chemicals, Inc.) as a solid acid catalyst and the mixture was reacted at 280° C. with stirring for 10 hours while flowing nitrogen (7000 mL/min.) in the system. The conversion rate of alcohol after the reaction was finished was 100% and purity of an alkene having 18 carbon atoms was 98.2%. The obtained crude alkene was transferred to a distilling flask to distill at 148 to 158° C./0.5 mmHg, thereby obtaining an alkene having 18 carbon atoms and purity of 100%. The distribution of double bond in the obtained alkene was as follows: C1-position: 0.8% by mass, C2-position: 31.3% by mass, C3-position: 22.9% by mass, C4-position: 15.5% by mass, C5-position: 10.8% by mass, C6-position: 7.2% by mass, C7-position: 5.3% by mass, and C8-position+C9-position: 6.2% by mass.

(3) Production of an Alkenyl Sulfonate and Hydroxyalkyl Sulfonate

Production Example 1

The alkene (content of an alkene with a double bond at C2-position is 16.5% by mass) having 16 carbon atoms which was obtained in Production Example A was charged in a thin-film type sulfonating reactor with an outer jacket and sulfur trioxide gas was flowed in the reactor and 20° C. cooling water was flowed through the reactor outer jacket to undergo a sulfonation reaction. The mole ratio of $SO_3$/alkene in the sulfonation reaction was set to 1.09. The obtained sulfonated product was added in an aqueous alkali solution adjusted by sodium hydroxide in an amount of 1.5 mol equivalent to theoretical acid value to neutralize at 30° C. for 1 hr with stirring. The neutralized product was heated at 160° C. for 1 hr in an autoclave to hydrolyze, thereby obtaining a sodium sulfonate crude product having 16 carbon atoms. 300 g of the crude product was transferred to a separatory funnel, to which 300 mL of ethanol was then added and then 300 mL of petroleum ether was added at a time to extract and remove oil-soluble impurities. At this time, inorganic compounds (major component: mirabilite) precipitated at the oil-water interface by the addition of ethanol was also removed from an aqueous phase by an oil-water separation operation. This extraction and removing operation was performed three times. The aqueous-phase side was evaporated to dryness to obtain sodium sulfonate having 16 carbon atoms. The ratio by mass of an alkenylsulfonate to a hydroxyalkyl sulfonate in the obtained sodium sulfonate was 19/81. Also, the content of a raw material alkene contained in the obtained sample was less than 100 ppm (less than the detection limit of GC) and the content of inorganic compounds was 1.3% by mass.

Production Example 2

Sodium sulfonate having 18 carbon atoms was obtained from the alkene (content of an alkene with a double bond at C2-position is 16.9% by mass) having 18 carbon atoms which was obtained in Production Example B, in the same condition as in Production Example 1.

The ratio by mass of an alkenylsulfonate to a hydroxyalkyl sulfonate in the obtained sodium sulfonate having 18 carbon atoms was 20/80. Also, the content of a raw material alkene contained in the obtained sample was less than 100 ppm (less than the detection limit of GC) and the content of inorganic compounds was 1.7% by mass.

Production Example 3

Sodium sulfonate having 16 carbon atoms was obtained from the alkene (content of an alkene with a double bond at C2-position is 30.4% by mass) having 16 carbon atoms which was obtained in Production Example C in the same condition as in Production Example 1.

The ratio by mass of an alkenylsulfonate to a hydroxyalkyl sulfonate in the obtained alkene sodium sulfonate was 10/90. Also, the content of a raw material alkene contained in the obtained sample was less than 100 ppm (less than the detection limit of GC) and the content of inorganic compounds was 1.9% by mass.

Production Example 4

Sodium sulfonate having 18 carbon atoms was obtained from the alkene (content of an alkene with a double bond at C2-position is 31.3% by mass) having 18 carbon atoms which was obtained in Production Example D, in the same condition as in Production Example 1. The ratio by mass of an alkenylsulfonate to a hydroxyalkyl sulfonate in the obtained sodium sulfonate having 18 carbon atoms was 20/80. Also, the content of a raw material alkene contained in the obtained sample was less than 100 ppm (less than the detection limit of GC) and the content of inorganic compounds was 0.9% by mass.

(II) Production of Component (B)

(1) Measuring Condition

In the present invention, the alkyl composition of an alkyl ether carboxylic acid, EO addition mole distribution, and the ratio of each component were measured by gas chromatography (GC) according to the following analytical methods.

[GC Analysis Condition]
GC instrument: trade name: 7890A, manufactured by Agilent Technologies Inc.
Column: trade name DB-5 (30 m, inside diameter: 0.25 mm, film thickness: 0.25 μm), manufactured by Agilent Technologies Inc.
Detector: FID
Carrier: helium gas, 1 mL/min.
Temperature rise condition: temperature was raised at 5° C./min. from 100° C. to 325° C. After that, the temperature was kept at 325° C. for 35 minutes.

[Method for Pretreatment of a Sample]
150 mg of an alkyl ether carboxylic acid was dissolved in 50 mL of methanol. Also, with regard to a cleansing composition, it was weighed to contain 150 mg of the alkyl ether carboxylic acid and dissolved in 50 mL of methanol. In this case, when the cleansing composition contained a strongly anionic surfactant such as a polyoxyethylene alkyl ether sulfate, it was weighed such that the amount of these materials was 250 mg or less. 1 mL of this solution was extracted and applied to a solid phase cartridge (trade name: Isolute SAX, manufactured by Biotage Japan Co., Ltd., 1 g, 3 mL, 500-0100-B) which was conditioned with 4 mL of methanol in advance to collect a passed solution in a 10 mL round bottom test tube. After that, the solution was eluted with 6 mL of a solution prepared by adding 4.6 g of formic acid in 100 mL of methanol and the eluate was also collected in the same test tube. The collected solution was put in a block heater kept at 50° C. and nitrogen gas was blown into the collected solution to concentrate the solution to a volume of about 1 mL. Then, nitrogen gas was further blown into the concentrated solution to dry. 2 mL of a diazomethane ether solution was added to the dried sample and was then allowed to stand at ambient temperature for 10 minutes with stirring to make a derivative. After that, nitrogen gas was blown into the dried solution at ambient temperature to concentrate the solution to a volume of 500 μL or less, to which was then added chloroform to be a volume of 500 μL and the resulting solution was subjected to GC analysis.

In this case, the diazomethane-ether solution was prepared using a diazomethane generator (trade name: GM-50, manufactured by Miyamoto Riken Ind. Co. Ltd.) in the following procedures. A first receiver was connected with a second receiver and the second receiver was connected with a third receiver by a silicon rubber stopper and a Teflon (trademark) tube. 0.8 g of N-methyl-N'-nitro-N-nitrosoguanidine was taken in the second receiver, in which 2.5 mL of ion exchange water was then added. 10 mL of t-butyl methyl ether was taken in the third receiver. The first, second, and third receivers were ice-cooled. In succession, a plastic syringe was set to the second receiver and 3 mL of a solution prepared by dissolving 20 g of sodium hydroxide in 100 mL of ion exchange water was poured into the syringe. This aqueous sodium hydroxide solution was gradually added dropwise in the second receiver to generate diazomethane gas and nitrogen gas was blown gently from the first receiver side to dissolve the diazomethane gas in t-butyl methyl ether contained in the third receiver, thereby obtaining a diazomethane ether solution.

As the reagents in the pretreatment of the above sample, the following compounds were used.
Methanol (manufactured by Kanto Chemical Co., Inc., for high-performance liquid chromatography, 25183-1B)
Formic acid (manufactured by Wako Pure Chemical Industries, Ltd., special grade chemical, 066-00461)
Chloroform (manufactured by Kanto Chemical Co., Inc., Cica First Class, 07278-01)
N-methyl-N'-nitro-N-nitrosoguanidine (manufactured by Kanto Chemical Co., Inc., Cica First Class, 25596-51)
t-butyl methyl ether (manufactured by Kanto Chemical Co., Inc., Cica Special Class, 04418-00)
Sodium hydroxide (manufactured by Wako Pure Chemical Industries, Ltd., special grade chemical, 196-13761)

(2) Production of an Alkyl Ether Carboxylic Acid

Production Example 5

A stainless autoclave equipped with a stirring and temperature control system was charged with 1144 g (6.14 mol) of lauryl alcohol (trade name: Kalcol 2098, manufactured by Kao Corporation), 60.2 g (0.281 mol) of myristyl alcohol (trade name: Kalcol 4098, manufactured by Kao Corporation), and 2.68 g (0.0478 mol) of potassium hydroxide and the mixture was dewatered under reduced pressure. Then, 996 g (22.6 mol) of ethylene oxide (EO) was introduced into the mixture at 155° C. to react at a temperature 155° C. under a pressure 0.4 MPa for 2 hours. After the reaction was finished, the reaction solution was stirred at 00° C. under a pressure reduced to 6 kPa for 30 minutes to remove unreacted ethylene oxide. Then, nitrogen was introduced into the system to raise the pressure to normal pressure and 4.82 g (0.0482 mol) of 90% lactic acid was added in the autoclave and the resulting solution was stirred at 80° C. for 30 minutes to obtain an alkylethoxylate (hereinafter referred also to as "product AE") having an EO addition mole number of 3.55 mol.

A glass reaction container equipped with a stirring system, a temperature control system, and an oxygen gas introduction pipe was charged with 90 g (0.2 mol) of the above product, 16.7 g (0.2 mol as sodium hydroxide) of an aqueous 48% sodium hydroxide solution, 0.9 g of palladium-platinum-bismuth type catalyst (4% of palladium, 1% of platinum, and 5% of bismuth were carried on activated carbon, water content: 50%), and 494.4 g of water. The temperature of the mixture solution was raised to 70° C. with stirring to undergo a catalytic oxidation reaction at 70° C. for 3.5 hours while blowing oxygen at a rate of 27 mol % (based on produced AE/hr). The rate of reaction was 89%.

After the reaction was finished, the catalyst was separated from the reaction solution by filtration to obtain an aqueous solution of sodium alkyl ether carboxylate. In succession, 35% hydrochloric acid was added to perform a separatory operation, thereby obtaining an alkyl ether carboxylic acid. This alkyl ether carboxylic acid is called EC1.

In the formula (1) representing EC1, as a result of gas chromatographic analysis, X=H, $R^1$ was a mixture of lauryl group/myristyl group=95/5, average carbon number: 12.1, the average of ns was 2.8, and EC1 contained a component (n=0) in an amount of 14.7% by mass and components (n=1 and 2) in a total amount of 36.1% by mass.

Also, the ratio of each component differing in EO addition mole number was calculated from the value of a component which is contained at a highest amount in the composition of $R^1$, and as a result, (mass of the component (n=0)):(mass of the component (n=1)):(mass of the component (n=2)):(mass of the component (n=3)):(mass of the component (n=4))=1:1.22:1.23:1.06:0.83.

EXAMPLES

Examples 1 to 22, Comparative Examples 1 and 2

Skin cleansing compositions as shown in Tables 3 to 6 were produced to evaluate foaming, foam volume, foam qualities, and feeling in rinsing, less stickiness when a towel-dry was finished, and skin feeling to the touch after dried. The results are shown together in Tables 3 to 6.

In this case, the structure of component (B) used in the examples are as shown in Tables 1 and 2.

Also, an average EO addition mole number of a commercially available alkyl ether carboxylic acid (AKYPO RLM 45CA (manufactured by Kao Corporation) was determined on referring to the specifications in a catalogue of a sales agency and publication on the website. An uncertain composition of alkyl, the amount of a component (n=0), and the total amount of components (n=1 and n=2) were analyzed according to the above method.

[Production Method]

All components excluding component (D) and aqueous sodium hydroxide solution were weighed and introduced into a beaker and heated to 80° C. to dissolve completely. After that, an aqueous 48% sodium hydroxide solution was added in such an amount as to obtain a desired degree of neutralization. The mixture was stirred for 30 minutes. When formulating component (D), it was added here, and the mixture was uniformed. After that, the resulting mixture was cooled to 30° C. to obtain an intended skin cleansing composition.

[Method of Evaluation]

1 g of each skin cleansing composition was picked on a hand and diluted about 5-fold with 30° C. tap-water to lightly foam the cleansing composition with both hands, thereby evaluating the condition of foaming, foam volume, and foam qualities (creamy feeling). After that, the foam was gathered on the palm of one hand to wash the other arm (from the elbow to the wrist). While washing the arm, the other arm was rubbed by the palm of the one hand to evaluate a feeling in rinsing. Less stickiness when the skin was dried just after wiped with a towel was evaluated by touching the inside of the arm with the palm of the one hand. Moreover, a sense of feeling when touching the skin with the palm of the one hand after the skin was dried was evaluated.

Each evaluation was made according to the following standards. The results are shown as an average of the evaluations of six expert panelists.

(1) Foaming:
  5: sensed that foaming was very good.
  4: sensed that foaming was good.
  3: sensed that foaming was normal.
  2: sensed that foaming was somewhat unacceptable.
  1: sensed that foaming was unacceptable.
(2) Foam volume:
  5: sensed that foam volume was very large.
  4: sensed that foam volume was large.
  3: sensed that foam volume was normal.
  2: sensed that foam volume was somewhat small.
  1: sensed that foam volume was small.
(3) Foam qualities (creamy feeling)
  5: sensed that foam was fine-texture and very creamy and therefore had good foam qualities.
  4: sensed that foam was creamy and therefore had good foam qualities.
  3: sensed that foam had somewhat creamy foam qualities.
  2: sensed that foam had slightly light and coarse foam qualities.
  1: sensed that foam had light and coarse foam qualities.
(4) Feeling in rinsing
  5: squeaky feeling like that of soap suddenly appears and strongly felt in rinsing.
  4: squeaky feeling like that of soap is felt in rinsing.
  3: slightly squeaky feeling is felt and reduced slimy feeling in rinsing.
  2: no squeaky feeling and slimy feeling is felt in rinsing.
  1: no squeaky feeling and strongly slimy feeling in rinsing.
(5) Less stickiness just when a towel-dry was finished
  5: sensed that stickiness when the skin was dried was very small.
  4: sensed that stickiness when the skin was dried was small.
  3: sensed that there was stickiness when the skin was dried.
  2: sensed that stickiness when the skin was dried was somewhat strong.
  1: sensed that stickiness when the skin was dried was very strong.
(6) Skin feeling to the touch after dried:
  5: skin after dried exhibits a silk-like high-quality feeling in which a moist feeling and a slippery feeling are compatible with each other,
  4: skin after dried exhibits a slightly silk-like moist feeling and a slippery feeling.
  3: skin after dried exhibits a slightly moist feeling and slippery feeling.
  2: skin after dried exhibits a slightly taut feeling.
  1: skin after dried exhibits a taut feeling.

TABLE 1

|  | R1 (mass %) | | | | Average carbon number | Average EO addition mole | n = 0 content | n = 1, 2 total content |
| --- | --- | --- | --- | --- | --- | --- | --- | --- |
|  | C10 | C12 | C14 | C16 | | | | |
| EC1 | 0 | 95 | 5 | 0 | 12.1 | 2.8 | 14.7% | 36.1% |

TABLE 2

|  | R1 (mass %) | | | | Average carbon number | Average EO addition mole | n = 0 content | n = 1, 2 total content |
| --- | --- | --- | --- | --- | --- | --- | --- | --- |
|  | C10 | C12 | C14 | C16 | | | | |
| 45CA ※1 | 0 | 68 | 26 | 6 | 12.8 | 4.5 | 9.6% | 31.2% |

※1 Effective component of AKYPO RLM 45CA

TABLE 3

| Component (mass %) | Examples | | | | Comp. Example |
| --- | --- | --- | --- | --- | --- |
|  | 1 | 2 | 3 | 4 | 1 |
| A Sulfonate (Production Example 3) | 10 | | | | 10 |
| Sulfonate (Production Example 4) | | 10 | | | |
| Sulfonate (Production Example 1) | | | 10 | | |
| Sulfonate (Production Example 2) | | | | 10 | |
| B EC1 (Production Example 5) | 10 | 10 | 10 | 10 | |
| C Purified water | Balance | Balance | Balance | Balance | Balance |
| Polyoxyethylene (4.5)lauryl ether carboxylic acid #1) | | | | | 10 |
| Aqueous sodium hydroxide solution (48%) | 1.37 | 1.37 | 1.37 | 1.37 | 1.37 |
| Total | 100 | 100 | 100 | 100 | 100 |
| C16/C18 | 6.2 | 6.2 | 6.2 | 6.2 | 6.2 |
| (a1)/(a2) | 10/90 | 20/80 | 19/81 | 20/80 | 10/90 |
| A/B | 1/1 | 1/1 | 1/1 | 1/1 | |
| Foaming | 2.5 | 2.5 | 3.0 | 2.5 | 2.0 |
| Foam volume | 2.5 | 2.5 | 3.0 | 2.5 | 2.0 |
| Foam qualities | 2.5 | 2.5 | 3.0 | 3.5 | 2.5 |
| Feeling in rinsing | 2.5 | 3.0 | 3.0 | 4.0 | 2.0 |
| Less stickiness when towel-dry is finished | 3.0 | 3.0 | 3.0 | 3.0 | 3.0 |
| Skin feeling to the touch after dried | 3.0 | 3.0 | 3.0 | 3.0 | 2.5 |

1) Effective component of AKYPO RLM 45CA (manufactured by Kao Corporation)

TABLE 4

| Component (mass %) | | Examples | | | | | | Comp. Example |
|---|---|---|---|---|---|---|---|---|
| | | 5 | 6 | 7 | 8 | 9 | 10 | 2 |
| A | Sulfonate (Production Example 1) | 16 | 10 | 4 | | | | |
| | Sulfonate (Production Example 2) | | | | 16 | 10 | 4 | |
| B | EC1(Production Example 5) | 4 | 10 | 16 | 4 | 10 | 16 | 10 |
| C | Purified water | Balance | Balance | Balance | Balance | Balance | Balance | Balance |
| | Sodium polyoxyethylene(2) lauryl ether sulfate #2) | | | | | | | 10 |
| | Aqueous sodium hydroxide solution (48%) | 0.55 | 1.37 | 2.19 | 0.55 | 1.37 | 2.19 | 1.37 |
| | Total | 100 | 100 | 100 | 100 | 100 | 100 | 100 |
| | pH | 6.2 | 6.2 | 6.2 | 6.2 | 6.2 | 6.2 | 6.2 |
| | C16/C18 (a1)/(a2) | 19/81 | 19/81 | 19/81 | 20/80 | 20/80 | 20/80 | |
| | A/B | 8/2 | 5/5 | 2/8 | 8/2 | 5/5 | 2/8 | |
| | Foaming | 2.5 | 3.0 | 3.5 | 2.0 | 2.5 | 3.5 | 3.5 |
| | Foam volume | 2.5 | 3.0 | 3.5 | 2.0 | 2.5 | 3.5 | 3.5 |
| | Foam qualities | 3.5 | 3.0 | 2.0 | 4.0 | 3.5 | 2.5 | 2.0 |
| | Feeling in rinsing | 3.5 | 3.0 | 2.0 | 4.0 | 4.0 | 3.5 | 2.0 |
| | Less stickiness when towel-dry is finished | 3.0 | 3.0 | 3.0 | 3.0 | 3.0 | 3.0 | 2.0 |
| | Skin feeling to the touch after dried | 3.0 | 3.0 | 3.0 | 3.5 | 3.0 | 3.0 | 2.0 |

2) Effective component of Emal 227 (manufactured by Kao Corporation)

TABLE 5

| Component (mass %) | | Examples | | |
|---|---|---|---|---|
| | | 11 | 12 | 13 |
| A | Sulfonate (Production Example 1) | 8 | 5 | 2 |
| | Sulfonate (Production Example 2) | 2 | 5 | 8 |
| B | EC1(Production Example 5) | 10 | 10 | 10 |
| C | Purified water | Balance | Balance | Balance |
| | Aqueous sodium hydroxide solution (48%) | 1.37 | 1.37 | 1.37 |
| | Total | 100 | 100 | 100 |
| | pH | 6.2 | 6.2 | 6.2 |
| | C16/C18 | 8/2 | 1/1 | 2/8 |
| | (a1)/(a2) | 19.2/80.8 | 19.5/80.5 | 19.8/80.2 |
| | A/B | 5/5 | 5/5 | 5/5 |
| | Foaming | 3.5 | 3.5 | 3.0 |
| | Foam volume | 3.5 | 3.5 | 3.0 |
| | Foam qualities | 3.0 | 3.5 | 3.5 |
| | Feeling in rinsing | 3 | 4.0 | 4.0 |
| | Less stickiness when towel-dry is finished | 3 | 3.0 | 3.0 |
| | Skin feeling to the touch after dried | 3.0 | 3.5 | 3.5 |

TABLE 6

| Component (mass %) | | Examples | | | | | | | | | |
|---|---|---|---|---|---|---|---|---|---|---|---|
| | | 12 | 14 | 15 | 16 | 17 | 18 | 19 | 20 | 21 | 22 |
| A | Sulfonate (Production Example 1) | 5.0 | 5.0 | 5.0 | 5.0 | 5.0 | 5.0 | 5.0 | 5.0 | 5.0 | 2.50 |
| | Sulfonate (Production Example 2) | 5.0 | 5.0 | 5.0 | 5.0 | 5.0 | 5.0 | 5.0 | 5.0 | 5.0 | 2.50 |
| B | EC1 (Production Example 5) | 10 | 10 | 10 | 10 | 10 | 10 | 10 | 10 | 10 | 5 |
| C | Purified water | Balance | Balance | Balance | Balance | Balance | Balance | Balance | Balance | Balance | Balance |
| D | Dimethyldiallyl-ammonium chloride/acrylamide (50:50) copolymer #3 | | 0.20 | | | | | | | | |
| | Hydroxyethyl cellulose hydroxypropyltrimethyl ammonium chloride ether #4 | | | 0.20 | | | | | | | |
| | Guar hydroxypropyl-trimonium chloride #5 | | | | 0.20 | | | | | | |
| | Dimethyldiallyl-ammonium chloride/acrylic acid/acrylamide (45:17:38) copolymer #6 | | | | | 0.20 | | | | | 0.2 |
| E | Glycerin mono-2-ethyl-hexyl ether #7 | | | | | | 1.0 | | | | 1.00 |

TABLE 6-continued

| Component (mass %) | | 12 | 14 | 15 | 16 | 17 | 18 | 19 | 20 | 21 | 22 |
|---|---|---|---|---|---|---|---|---|---|---|---|
| F | Laurylhydroxysulfobetaine #8) | | | | | | | 2.0 | | | |
| | Lauric acid amide propyl betaine #9) | | | | | | | | 2.0 | | 2.0 |
| | Alkyl (8-16) glucoside #10) | | | | | | | | | 2 | 2 |
| | Aqueous sodium hydroxide solution (48%) | 1.37 | 1.37 | 1.37 | 1.37 | 1.37 | 1.37 | 1.37 | 1.37 | 1.37 | 0.69 |
| | Aqueous malic acid solution (50%) | q.s. | q.s. | q.s. | q.s. | q.s. | q.s. | q.s. | q.s. | q.s. | q.s. |
| | Total | 100 | 100 | 100 | 100 | 100 | 100 | 100 | 100 | 100 | 100 |
| | pH | 6.2 | 6.2 | 6.2 | 6.2 | 6.2 | 6.2 | 6.2 | 6.2 | 6.2 | 6.2 |
| | C16/C18 | 1/1 | 1/1 | 1/1 | 1/1 | 1/1 | 1/1 | 1/1 | 1/1 | 1/1 | 1/1 |
| | (a1)/(a2) | 19.5/80.5 | 19.5/80.5 | 19.5/80.5 | 19.5/80.5 | 19.5/80.5 | 19.5/80.5 | 19.5/80.5 | 19.5/80.5 | 19.5/80.5 | 19.5/80.5 |
| | A/B | 5/5 | 5/5 | 5/5 | 5/5 | 5/5 | 5/5 | 5/5 | 5/5 | 5/5 | 5/5 |
| | D/(A + B) | | 0.010 | 0.010 | 0.010 | 0.010 | | | | | 0.010 |
| | Foaming | 3.5 | 3.5 | 3.5 | 3.5 | 3.5 | 4 | 3.5 | 3.5 | 3.5 | 4 |
| | Foam volume | 3.5 | 4 | 3.5 | 3.5 | 4 | 4 | 4 | 4 | 4 | 4.5 |
| | Foam qualities | 3.5 | 3.5 | 4 | 4 | 4 | 3.5 | 4 | 4 | 3.5 | 4 |
| | Feeling in rinsing | 4.0 | 4 | 4 | 4 | 4 | 4 | 4 | 4 | 4 | 4 |
| | Less stickiness when towel-dry is finished | 3.0 | 3 | 3 | 3 | 3 | 3.5 | 3 | 3 | 3 | 3.5 |
| | Skin feeling to the touch after dried | 3.5 | 4 | 4 | 4 | 4 | 3.5 | 3.5 | 3.5 | 3.5 | 4 |

3) Effective component of Marcoat 550 (manufactured by Lubrizol)
4) Effective component of UCARE POLYMER LR400 (manufactured by The Dow Chemical Company)
5) Jaguar C17 (manufactured by Rhodia)
6) Effective component of Marcoat Plus 3331 (manufactured by Lubrizol)
7) Effective component of Penetol GE-EH (manufactured by Kao Corporation)
8) Effective component of Anphitol 20HD (manufactured by Kao Corporation)
9) Effective component of Anphitol 20AB (manufactured by Kao Corporation)
10) Effective component AG-124 (manufactured by Kao Corporation)

What is claimed is:

1. A skin cleansing composition comprising the following components (A), (B), and (C):
   (A) (a1) an alkenylsulfonic acid having 12 to 22 carbon atoms or its salt, (a2) an alkylsulfonic acid having 12 to 22 carbon atoms or its salt, or a mixture of them,
   wherein in component (A), (a1) comprises at least one alkenylsulfonic acid which is a straight-chain hydrocarbon having a double bond and 12 to 22 carbon atoms and containing a sulfo-group on any one of the carbon atoms excluding terminal carbon atoms or its salt, and
   wherein in component (A), (a2) comprises at least one hydroxyalkylsulfonic acid having 12 to 22 carbon atoms and containing a sulfo-group on any one of the carbon atoms excluding terminal carbon atoms or its salt;
   (B) an alkyl ether carboxylic acid represented by the following formula (1) or its salt:

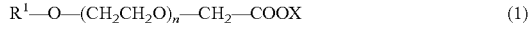

$$R^1-O-(CH_2CH_2O)_n-CH_2-COOX \quad (1)$$

wherein $R^1$ represents an alkyl group having 4 to 22 carbon atoms, n denotes a number from 0 to 20, X represents a hydrogen atom, an alkali metal, an alkali earth metal, ammonium, or organic ammonium, and n denotes a number of 0.5 or more and less than 4 on average; and
   (C) water.

2. The skin cleansing composition according to claim 1, wherein component (A) is contained in an amount of 0.1 to 60% by mass based on a total composition, and component (B) is contained in an amount of 0.1 to 30% by mass based on a total composition.

3. The skin cleansing composition according to claim 1, wherein in component (A), (a2) comprises at least one hydroxyalkylsulfonic acid which is a straight-chain hydrocarbon having 12 to 18 carbon atoms and containing a hydroxyl group on any one of the carbon atoms excluding terminal carbon atoms and containing a sulfo-group on any one of the carbon atoms excluding terminal carbon atoms or its salt.

4. The skin cleansing composition according to claim 1, wherein (a1) comprises an alkenylsulfonic acid having 16 or 18 carbon atoms or its salt.

5. The skin cleansing composition according to claim 1, wherein (a2) comprises at least one hydroxyalkylsulfonic acid having 16 or 18 carbon atoms or its salt.

6. The skin cleansing composition according to claim 1, wherein (a1) is a mixture of alkenylsulfonic acids having 16 and 18 carbon atoms or their salts, and the ratio by mass of the alkenylsulfonic acid having 16 carbon atoms or its salt to the alkenylsulfonic acid having 18 carbon atoms or its salt is 1/9 to 9/1.

7. The skin cleansing composition according to claim 1, wherein (a2) is a mixture of hydroxyalkylsulfonic acids having 16 and 18 carbon atoms or their salts, and the ratio by mass of the hydroxyalkylsulfonic acid having 16 carbon atoms or its salt to the hydroxyalkylsulfonic acid having 18 carbon atoms or its salt is 1/9 to 9/1.

8. The skin cleansing composition according to claim 1, wherein component (A) is a mixture of (a1) and (a2), and the ratio by mass of (a1) to (a2), (a1)/(a2), is 5/95 to 50/50.

9. The skin cleansing composition according to claim 1, wherein component (A) is
   a mixture of (a1) an alkenylsulfonic acid containing a sulfo-group on any one of the carbon atoms excluding terminal carbon atoms and having 16 carbon atoms or its salt, and (a2) a hydroxyalkylsulfonic acid which is a straight-chain hydrocarbon containing a hydroxyl group and having 16 carbon atoms and containing a sulfo-group on any one of the carbon atoms excluding terminal carbon atoms or its salt or;

a mixture of (a1) an alkenylsulfonic acid containing a sulfo-group on any one of the carbon atoms excluding terminal carbon atoms and having 18 carbon atoms or its salt and (a2) a hydroxyalkylsulfonic acid which is a straight-chain hydrocarbon containing a hydroxyl group and having 18 carbon atoms and containing a sulfo-group on any one of the carbon atoms excluding terminal carbon atoms or its salt.

10. The skin cleansing composition according to claim 1, wherein component (A) is a mixture of
   (a1) a mixture of alkenylsulfonic acids each containing a sulfo-group on any one of the carbon atoms excluding terminal carbon atoms and having 16 and 18 carbon atoms or their salts and
   (a2) a mixture of hydroxyalkylsulfonic acids which are each a straight-chain hydrocarbon containing a hydroxyl group and having 16 and 18 carbon atoms and each containing a sulfo-group on any one of the carbon atoms excluding terminal carbon atoms or their salts.

11. The skin cleansing composition according to claim 10, wherein component (A) is a mixture of
   (a1) a mixture of alkenylsulfonic acids each containing a sulfo-group on any one of the carbon atoms excluding terminal carbon atoms and having 16 and 18 carbon atoms or their salts, and
   (a2) a mixture of hydroxyalkylsulfonic acids which are each a straight-chain hydrocarbon containing a hydroxyl group and having 16 and 18 carbon atoms and each containing a sulfo-group on any one of the carbon atoms excluding terminal carbon atoms or their salts, and
   a ratio by mass of the hydrocarbon having 16 carbon atoms to the hydrocarbon having 18 carbon atoms is preferably 9/1 to 1/9, and the ratio by mass of (a1) to (a2) is 5/95 to 50/50.

12. The skin cleansing composition according to claim 1, wherein in the formula (1), n denotes a number from 0 to 20 and an average addition mole number (average of n) in the composition of component (B) is 0.5 or more and less than 4.

13. The skin cleansing composition according to claim 1, wherein component (B) comprises a component obtained when n=0 in the formula (I) in an amount of 9.9 to 27% by mass.

14. The skin cleansing composition according to claim 1, wherein component (B) is a mixture of components (n=0, 1, 2, 3 and 4) in the formula (1) and the components (n=0, 1, 2, 3, and 4) are contained at a ratio by mass of (mass of component (n=0)):(mass of component (n=1)):(mass of component (n=2)):(mass of component (n=3)):(mass of component (n=4)) being 1:0.99 to 3.50:0.89 to 3.00:0.76 to 3.00:0.63 to 1.6.

15. The skin cleansing composition according to claim 1, wherein component (B) comprises a component obtained when n=0 in the formula (1) in an amount of 9.9% by mass or more and less than 12% by mass and component (B) is a mixture of components (n=0, 1, 2, 3, and 4) in the formula (1) and the components are contained at a ratio by mass of (mass of component (n=0)):(mass of component (n=1)):(mass of component (n=2)):(mass of component (n=3)):(mass of component (n=4)) being 1:1.53 to 1.87:1.59 to 2.25:1.33 to 2.16:1.14 to 1.52, or component (B) comprises a component obtained when n=0 in the formula (1) in an amount of 12 to 17% by mass and component (B) is a mixture of components (n=0, 1, 2, 3, and 4) in the formula (I) and the components are contained at a ratio by mass of (mass of component (n=0)):(mass of component (n=1)):(mass of component (n=2)):(mass of component (n=3)):(mass of component (n=4)) being 1:0.99 to 1.34:0.89 to 1.40:0.76 to 1.23:0.63 to 0.99.

16. The skin cleansing composition according to claim 1, further comprising (D) a cationic group-containing polymer and the polymer is contained in an amount of 0.01 to 2% by mass in a total composition.

17. The skin cleansing composition according to claim 16, wherein a ratio by mass of component (D) to a total mass of components (A) and (B) (where the mass of component (A) indicates the mass when component (A) is in the form of a salt and the mass of component (B) indicates the mass when component (B) is in the form of an acid), (D)/((A)+(B)), is 0.001 to 0.05.

18. A skin washing method comprising applying the skin cleansing composition as claimed in claim 1 to wash the skin, followed by rinsing the skin.

* * * * *